United States Patent [19]

Borsanyi et al.

[11] Patent Number: 4,493,706
[45] Date of Patent: Jan. 15, 1985

[54] LINEAR PERISTALTIC PUMPING APPARATUS AND DISPOSABLE CASETTE THEREFOR

[75] Inventors: Alexander S. Borsanyi, Newport Beach; Donald E. Bobo, Fountain Valley, both of Calif.

[73] Assignee: American Hospital Supply Corporation, Evanston, Ill.

[21] Appl. No.: 407,440

[22] Filed: Aug. 12, 1982

[51] Int. Cl.³ .............................................. A61M 5/00
[52] U.S. Cl. ........................... 604/153; 128/DIG. 12; 417/477
[58] Field of Search ............................. 128/DIG. 12; 604/151-153, 34, 250; 417/474, 475, 477

[56] References Cited

U.S. PATENT DOCUMENTS

| | | | |
|---|---|---|---|
| 1,874,667 | 8/1932 | Wada . | |
| 2,249,806 | 7/1941 | Bogoslowsky | 103/149 |
| 2,412,397 | 12/1946 | Harper | 417/474 |
| 2,414,355 | 1/1947 | Bogoslowsky | 103/149 |
| 2,483,924 | 10/1949 | Moulinier | 604/153 X |
| 2,722,893 | 11/1955 | Maillot | 103/148 |
| 3,067,692 | 12/1962 | Brkich | 103/149 |
| 3,083,647 | 4/1963 | Muller | 103/148 |
| 3,229,643 | 1/1966 | Roudaut | 103/149 |
| 3,233,553 | 2/1966 | Chanton | 103/149 |
| 3,582,234 | 6/1971 | Isreeli et al. | 604/153 X |
| 3,609,069 | 9/1971 | Martinelli | 417/474 |
| 3,675,653 | 7/1972 | Crowley et al. | 604/153 X |
| 3,927,955 | 12/1975 | Spinosa | 417/477 |
| 3,981,633 | 9/1976 | Wall | 417/474 |
| 3,990,444 | 11/1976 | Vial | 604/153 X |
| 4,187,057 | 2/1980 | Xanthopoulos | 417/63 |
| 4,191,184 | 3/1980 | Carlisle | 128/214 |
| 4,199,307 | 4/1980 | Jassawalla | 417/474 |
| 4,256,437 | 3/1981 | Brown | 417/45 |
| 4,273,121 | 6/1981 | Jassawalla | 128/214 |
| 4,373,525 | 2/1983 | Kobayashi | 417/474 X |

Primary Examiner—Dalton L. Truluck
Attorney, Agent, or Firm—Tilton, Fallon, Lungmus

[57] ABSTRACT

A linear peristaltic pump, and a disposable casette therefor, particularly suitable for the infusion of parenteral fluids. The pump includes a housing having a power-driven shaft and a series of small bearing assemblies having their inner members eccentrically mounted upon that shaft. A thin elastomeric membrane extends along the series of bearing assemblies for engagement with the outer members thereof along a first band or linear zone of contact lying in the same plane as the axis of the shaft. The disposable casette is removably supported by the housing and takes the form of a rigid, planar, perimetric frame having an opening across which is stretched a section of elastomeric tubing. Locators provided by the housing and frame orient the casette with the axis of the tubing in the same plane as the first band of contact and the axis of the shaft, and a platen provided by the housing engages the section of elastomeric tubing that bridges the opening of the frame to urge that section into engagement with the opposite side of the membrane along a second band or linear zone of contact parallel with the first band of contact. The casette may include tubular extensions and connectors for connecting opposite ends of the section of elastomeric tubing to a source of fluid and to a patient.

16 Claims, 15 Drawing Figures

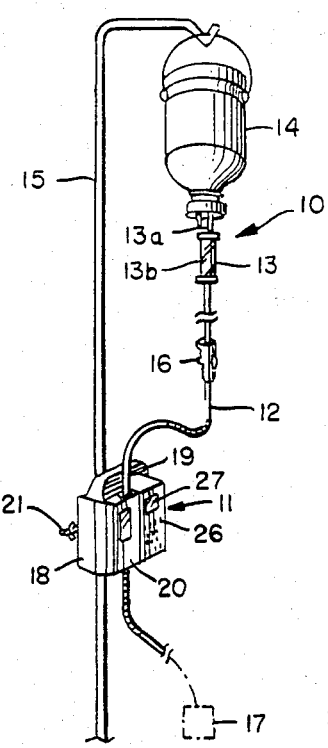
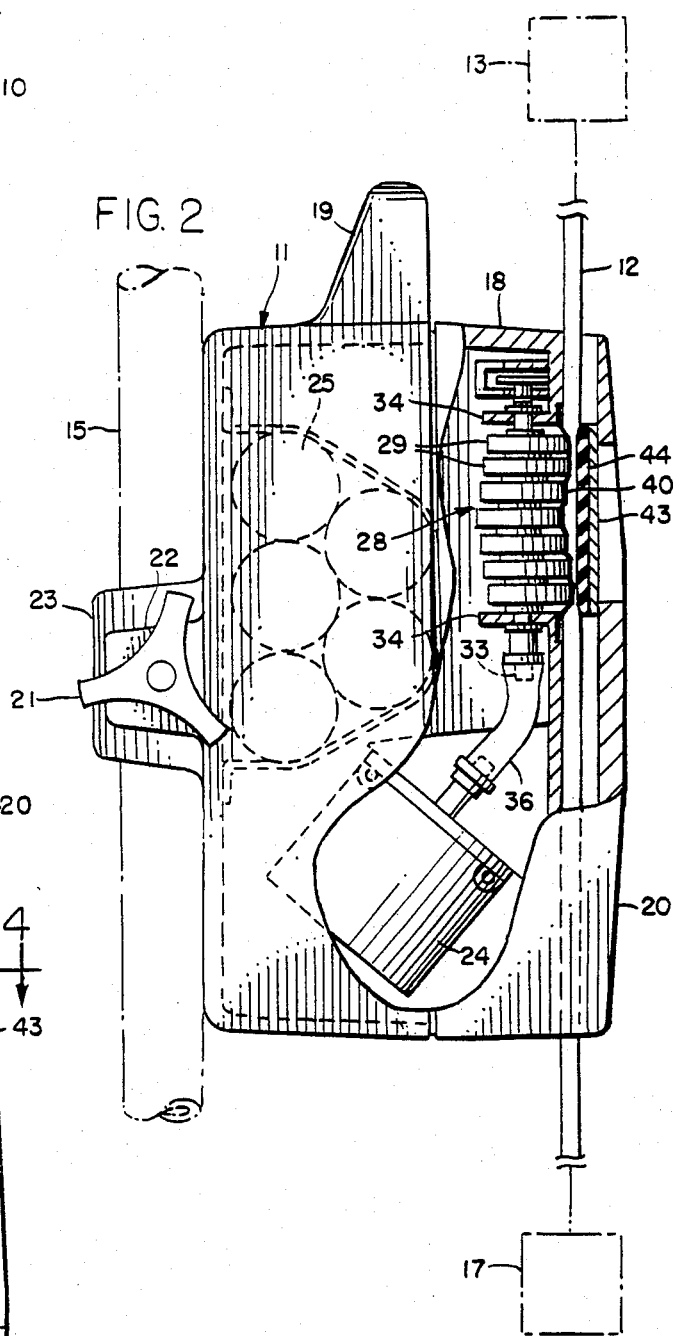
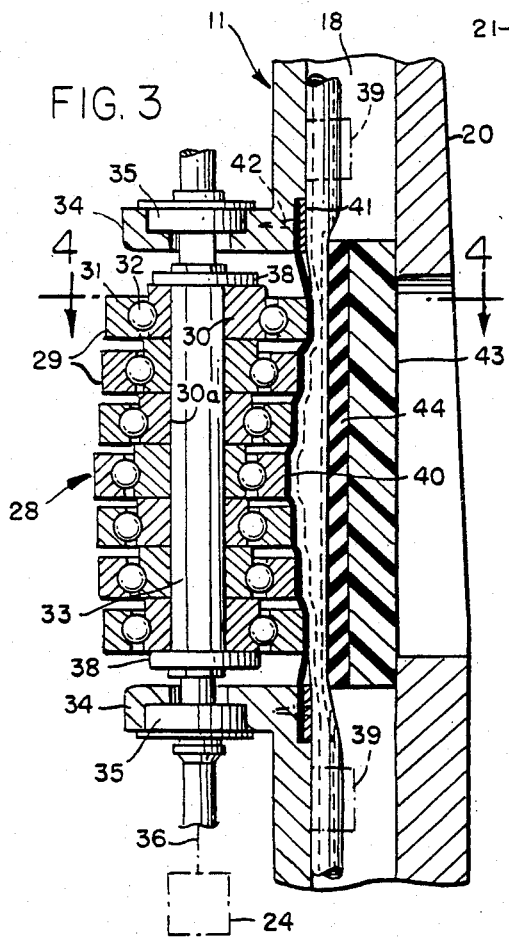
FIG. 1
FIG. 2
FIG. 3

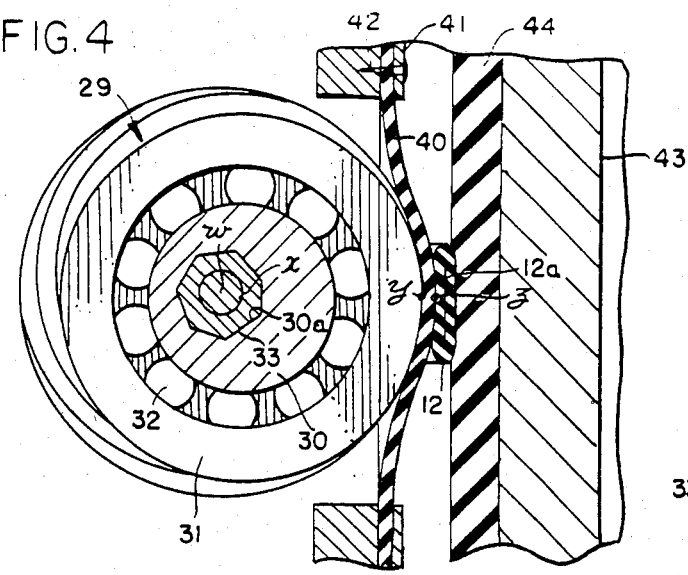
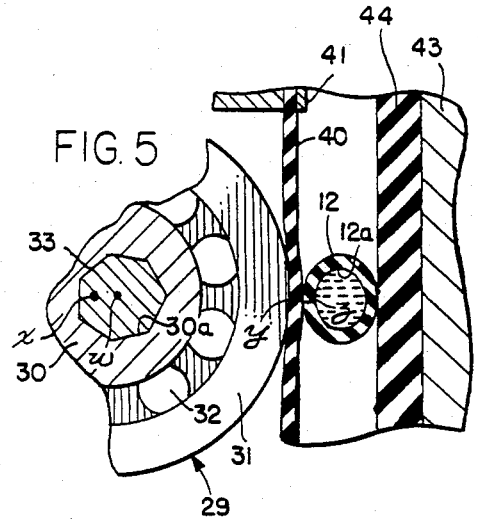
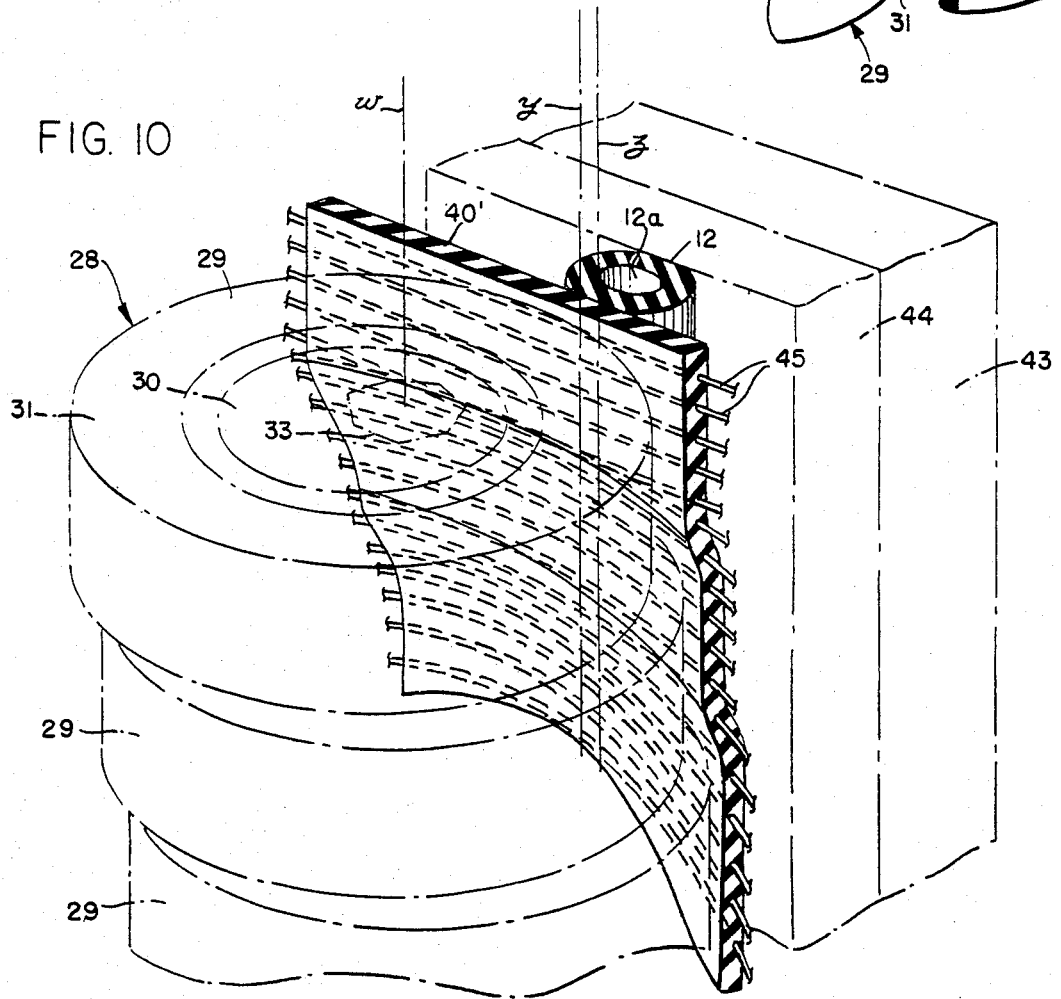

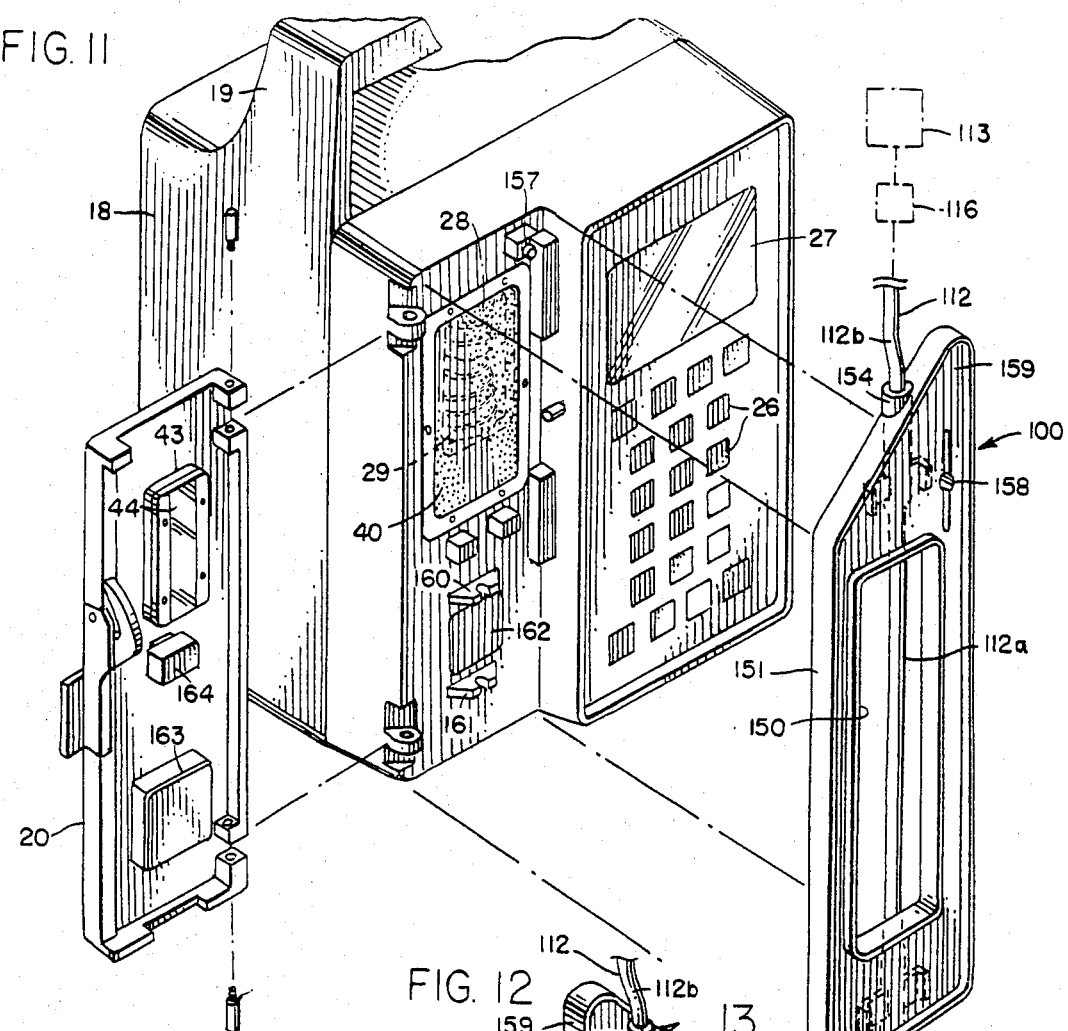
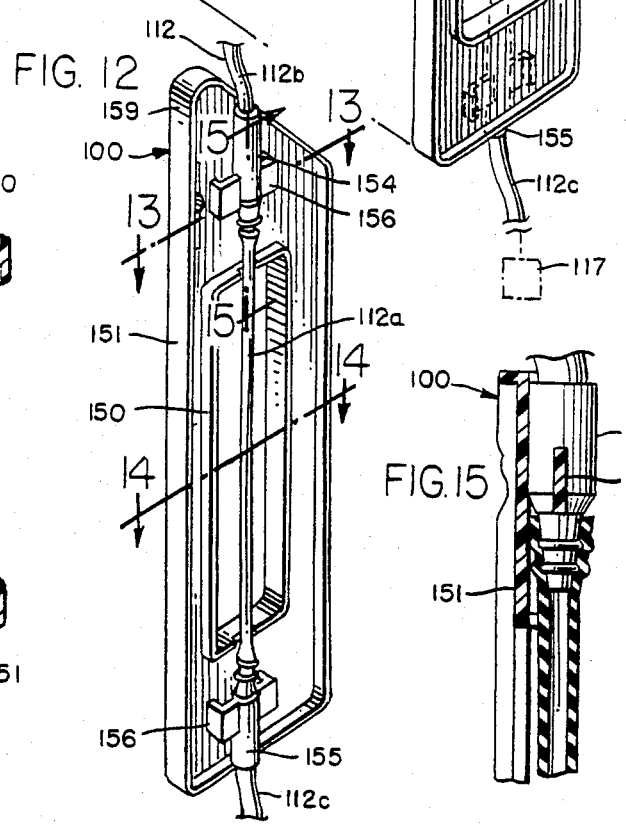
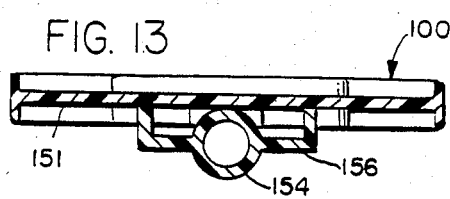
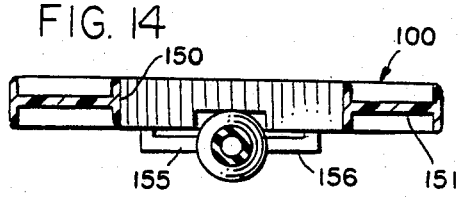
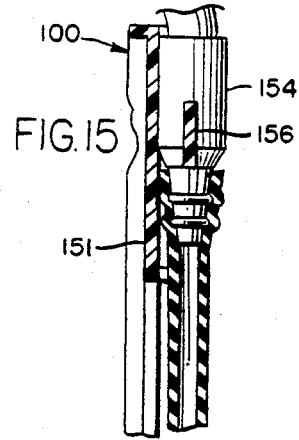

LINEAR PERISTALTIC PUMPING APPARATUS AND DISPOSABLE CASETTE THEREFOR

BACKGROUND

Peristaltic pumps of the type known for use for the infusion of medical fluids, or for the removal of body fluids, are generally characterized by a length of flexible tubing which is disposed within an arc between a stator-like member and a rotor assembly. The rotor assembly is provided with a plurality of rollers which, upon rotation of the rotor assembly, successively pinch-off the tube and advance the location of the pinch-off so as to progressively advance the fluid within the tube at a rate determined by the rate of rotation of the rotor. Such pumps have the advantage of having a disposable element in the fluid flow path, in that the length of tubing in the pump may be replaced after each use, and casettes have been provided to facilitate the insertion and removal of such lengths of tubing. Patents illustrative of such constructions are U.S. Pat. Nos. 3,927,955, 4,256,437, and 4,187,057. Despite their advantages, such systems are also known to exhibit poor accuracy and reproducibility, require substantial power for operation (thereby making them relatively expensive and inappropriate for battery operation), be relatively complex and bulky in construction, and require a casette which, because it must support the tube along an arcuate path, is relatively elaborate, complex, and expensive.

U.S. Pat. Nos. 4,199,307 and 4,273,121 disclose linear casettes for medical infusion systems, the casettes comprising tubes having flexible portions which are engaged by movable bar members at three different locations to control flow of fluid through the tubes. The use of pressure bars is also disclosed in U.S. Pat. No. 3,083,647.

Other patents such as U.S. Pat. Nos. 3,229,643, 3,981,633, and 3,233,553 disclose pumps in which shafts and eccentrics are disposed internally rather than externally in relation to the flexible tubes. Other patents generally illustrative of the state of the art are U.S. Pat. Nos. 3,067,692, 2,722,893, 1,874,667, 2,414,355, and 2,249,806.

SUMMARY OF THE INVENTION

This invention is directed to a linear peristaltic pump system in which a casette having a rigid, planar perimetric frame and a tensioned linear section of elastomeric tubing bridging the opening of that frame coacts with the other elements of the system to deliver fluid at accurate, preselected, and reproducible flow rates. In addition, the casette has the advantages of being relatively simple and inexpensive in construction, and is easily and quickly inserted and removed from the pump housing. In the operation of the pump, the tensioned section of tubing that spans the opening of the casette frame is interposed between a platen and an elastomeric membrane, both of which are provided by the pump housing. The elastomeric membrane engages the outer members or races of a series of bearing assemblies eccentrically mounted upon a power-driven shaft, the membrane engaging the bearing assemblies along a first band or linear zone of contact lying in the same plane as the rotational axis of the shaft. The elastomeric tubing of the casette engages the opposite side of the membrane along a second band or linear zone of contact lying in the same plane and parallel with the first line of contact. Replacement of a casette may be achieved simply by withdrawing the platen, which may be carried by a door of the housing assembly, and withdrawing the casette and its elastomeric tubing from contact with the membrane that overlies the bearing assemblies.

In a preferred embodiment particularly suitable for the administration of parenteral fluids, the casette takes the form of a generally rectangular perimetric frame having an elongated rectangular opening. Attachment sleeves face each other from opposite edges of that opening, and the section of tensioned elastomeric tubing has its ends secured to the attachment sleeves so that the tubing section bridges the full length of the opening. The casette may include other tubing sections secured to and communicating with the attachment sleeves, the other sections being provided at their free ends with suitable coupling elements for connecting the casette to a patient and a source of parenteral fluid.

Other features, advantages, and objects of the invention will become apparent from the specification and drawings.

DRAWINGS

FIG. 1 is a perspective view of a system utilizing the peristaltic fluid-pumping apparatus of the invention for metered intravenous (IV) administration.

FIG. 2 is a side elevation taken partly in section showing the pump apparatus.

FIG. 3 is an enlarged vertical sectional view showing details of the apparatus.

FIG. 4 is a still further enlarged horizontal sectional view taken along line 4—4 of FIG. 3 and showing the eccentric bearing assembly in an extreme position compressing and occluding the elastomeric tube.

FIG. 5 is a horizontal sectional view similar to FIG. 4 but showing the bearing assembly in its outer extreme position with the elastomeric tube nearly fully expanded.

FIG. 10 is a fragmentary perspective view of the apparatus modified to include a membrane preferentially reinforced against stretching in directions transverse to the axis of the tube.

FIG. 11 is a fragmentary perspective view of a pump apparatus modified to utilize a replaceable casette for supporting the fluid delivery tube.

FIG. 12 is a perspective view showing the opposite side of the casette depicted in FIG. 10.

FIG. 13 is an enlarged cross sectional view taken along line 13—13 of FIG. 12.

FIG. 14 is an enlarged sectional view along line 14—14 of FIG. 12.

FIG. 15 is an enlarged longitudinal sectional view along line 15—15 of FIG. 12.

DETAILED DESCRIPTION

Figure 6:
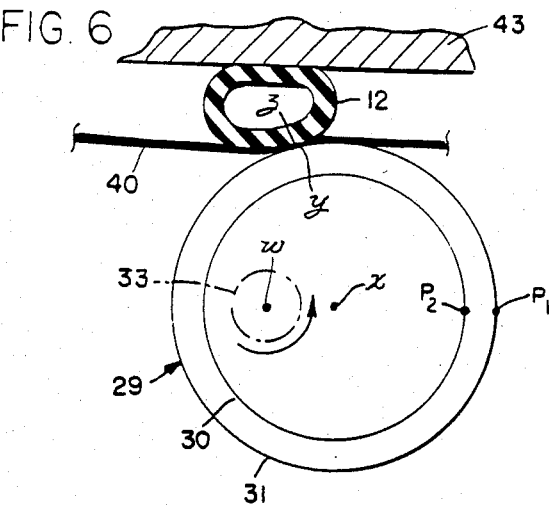
FIGS. 6–9 are schematic views showing the sequence of operation of a modified fluid-pumping apparatus.
Figure 7:
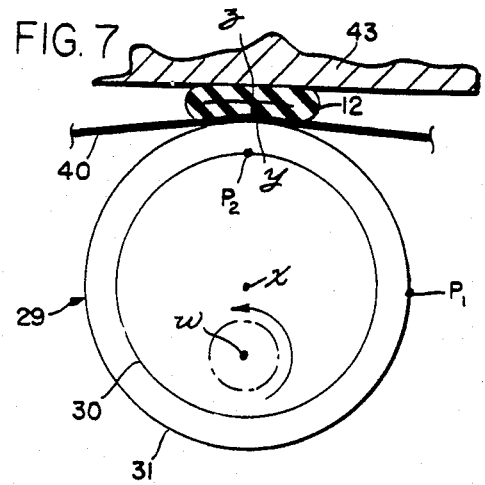

Referring to the drawings, and particularly to FIGS. 1-9, the numeral 10 generally designates an apparatus including a metering pump 11, a fluid delivery tube 12, coupling means 13 for coupling one end of the tube to a suitable container 14, in this case a parenteral solution container supported by a conventional IV stand 15. The coupling means takes the form of a spike 13a formed as part of drip chamber housing 13b and received within the opening of a vent-providing stopper at the mouth of the container. A suitable valve or clamp 16 may be provided for controlling or interrupting the flow of fluid through tube 12.

The opposite end of the tube 12 leads to a suitable connector 17 represented diagramatically in FIGS. 1 and 2. In the case of a fluid administration system, the connector would ordinarily take the form of a hypodermic needle or cannula. Excluding metering pump 11, the elements of the system shown in FIGS. 1-2 are conventional and well known and, therefore, further discussion of such elements is believed unnecessary herein.

The metering pump 11 includes a housing 18 equipped with a handle 19 and a door or removable panel 20. Attachment of the housing to IV stand 15 is achieved by thumb screw 21 which can be tightened against the pole of the stand when the pole extends between a pair of ears 22, 23 projecting from the rear of the housing. An electric stepping motor 24 drives the pump and a power pack 25 composed of one or more batteries or power cells (5 are shown) is located within the housing to supply power for the motor and other components. The electrical controls for the operation of the motor may be simple or complex depending on the requirements and use of the system. In the illustration given, a plurality of finger buttons 26 are provided at the face of the housing and a digital display window 27 reveals information concerning selected delivery rates as controlled by motor speed for a tube 12 of selected cross sectional dimensions.

The pump mechanism 28 includes a series of bearing assemblies 29 each having inner and outer bearing members 30 and 31, respectively. Preferably the inner member 30 takes the form of an inner bearing race, the outer member 31 constitutes an outer race, and anti-friction bearing elements 32 are disposed therebetween. Such anti-friction bearing elements would normally consist of ball bearings; however, the use of various types of roller bearings is possible. Furthermore, other types of bearing assemblies, such as self-lubricating sleeve bearings, might be advantageously used.

Each inner race (or member) is mounted eccentrically upon a drive shaft 33. Journalling means in the form of hangers 34 and bearings 35 (preferably ball bearings) support the ends of drive shaft 33 as shown in FIGS. 2 and 3. One end of the shaft (the lower end in the embodiment illustrated) is operatively connected to motor 24. A flexible coupling 36 is shown for that purpose, but other connecting means may be used. Also, while the drive shaft 33 is illustrated with its longitudinal axis oriented vertically, it is to be understood that the action of the pump is independent of such orientation as long as fluid is available to the pump through line or tube 12.

Each inner race (or member) 30 is eccentrically mounted upon shaft 33 with the centers of all such races being equidistant from the axis w of the drive shaft and with the angular spacing between all of such centers being essentially the same and the sum of the angular spacing being 360°. Where a series of seven bearing assemblies is provided as shown, the incremental angular distance between the centers of the inner races should be 360° divided by seven, or approximately 51.43°. A greater or smaller number of bearing assemblies may be provided, although the preferred range is believed to be 3 to 30 such assemblies. Of particular importance is the fact that the series of bearing assemblies must be mounted upon the drive shaft 33 so that the centers x of the inner races describe a spiral or helix of at 360° about drive shaft axis w.

The inner races 30 may be secured upon the shaft 33 in any suitable manner. In the embodiment illustrated in the drawings, shaft 33 has a central portion of non-circular (heptagonal) cross sectional outline and the eccentrically-disposed openings 30a in the respective inner races 30 are of the same configuration so that the eccentric bearings may be incrementally positioned upon the shaft with their centers helically oriented. The inner races are thereby secured against independent relative rotation with respect to shaft 33, and locking elements 38 are secured to the shaft at opposite ends of the series of bearing assemblies 29 to hold the series against axial displacement.

The central portion of elastomeric tube 12 is supported with its longitudinal axis parallel with the rotational axis of the shaft 33 and with a linear zone of the outer surface of a membrane 40 in contact with the outer surfaces of outer races 31. Ideally the tube is stretched so that it is under slight axial tension, thereby assuring that the portion of the tube opposite the bearing assemblies will be straight or linear in the absence of lateral distorting forces. For purposes of such tensioning, and to insure parallel alignment of the tube with the axis w of the drive shaft, mounting straps or brackets may be located at 39 to immobilize those portions of the tube with respect to housing 18. Alternatively, such portions of the tube may be secured to the housing by adhesives or by any other suitable means.

The elastomeric imperforate membrane 40 is interposed between tube 12 and the cylindrical surfaces of outer bearing members or races 31, as shown most clearly in FIGS. 3-5. The membrane is planar in an untensioned state and assumes the configuration shown in FIG. 3 because of the distortions developed by bearing assemblies 29 and tubing 12. It bridges the space in which the series of bearing assemblies is located and separates that mechanism from tube 12. Any suitable means may be used to secure the periphery of the membrane to casing or housing 18; in the embodiment illustrated, a frame 41 is secured to the housing by screws 42 and clamps the perimeter of the membrane tightly in place.

A rigid platen 43 braces tube 12 and not only maintains the tube in contact with one surface of the membrane 40 but also maintains the opposite surface of the membrane in contact with the outer races of the bearing assemblies 29. More specifically, as shown in FIGS. 4 and 5, the outer races tangentially engage the membrane 40 along a first linear zone or band of contact y, and the elastomeric tube engages the opposite side of the membrane along a second linear zone or band of contact z directly behind or opposite from the first band of contact. Also, the two bands of contact y and z lie in the same plane as the rotational axis w of drive shaft 33.

Each bearing assembly 29 has its inner race 30 eccentrically mounted so that its center x moves between one extreme position in which center x is spaced maximally from the platen and the lumen 12a of the tube is substantially fully open (FIG. 5) and the other extreme position in which center x is spaced minimally from platen 43 and the lumen of the tube is closed (FIG. 4). To reduce torque peaks that develop as each bearing assembly sweeps through the tube-occluding position of FIG. 4, especially when two such assemblies (the first and last of the series) simultaneously compress and substantially close the tube, platen 43 may be provided with a resilient facing 44 engaging and supporting tube 12. The facing must not be so compliant that it will allow outward displacement of the tube in preference to complete occlusion of that tube. The tube should close as shown in FIG. 4 with the resilience of facing 40 serving the primary purpose of reducing the torque peak once such occlusion has taken place. Additionally, the resilient facing may perform the secondary function of providing additional resistance to lateral or transverse displacement of the portion of the tube 12 extending alongside the series of bearing assemblies 29 and membrane 40. In general, a facing material having a durometer of about 60 to 80 has been found effective.

Lateral displacement of the tube during pump operation is prevented primarily by membrane 40 and by the effectiveness of anti-friction bearing elements 32. A slight frictional resistance is necessarily inherent in the operation of each bearing assembly 29, but that resistance is substantially less than the frictional resistance between the outer surface of outer race 31 and the surface of membrane 40 in contact therewith. Tangential sliding movement between the outer races of the bearing assemblies and membrane 40 is therefore avoided. Since the membrane's resistance to stretching is substantial in relation to the frictional resistance inherent in the operation of the bearing assembly, rotational forces that might otherwise be transmitted to tube 12 are isolated by membrane 40.

In the form of the invention depicted in FIGS. 2-5, each outer race 31 remains in continuous contact with membrane 40 even when the center x of bearing assembly 29 is spaced maximally from the platen and the lumen of tube 12 is substantially fully open (FIG. 5). Alternatively, the apparatus may be adjusted or constructed so that it is structurally and functionally identical to what has already been described except that the outer race of each bearing assembly is momentarily drawn out of contact with the membrane when the shaft has rotated to space center x its maximum distance from the platen, in which case the outer race will be free to rotate a limited angular distance (i.e., 360° divided by the number of assemblies) until it is again brought into contact with the membrane. Such an embodiment not only provides the advantages of allowing the tube to expand to a fully open position (in which the cross section of the lumen is circular in outline) but also, by permitting incremental rotation of the outer race, tends to produce more uniform bearing wear and thereby increase the operating life of the apparatus.

The operation of such a modified version of the pump is schematically illustrated in FIGS. 6-9. The two concentric circles represent a bearing assembly 29 with the inner circle indicating the inner race or member 30 and the outer circle representing the outer race or member 31. The inner race is eccentrically mounted with the extent of eccentricity being the distance between the center x of the inner race and the rotational axis w of the mounting shaft.

Figure 8:
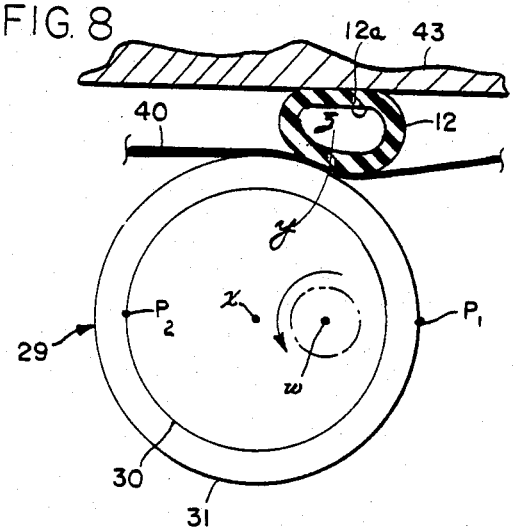
Figure 9:
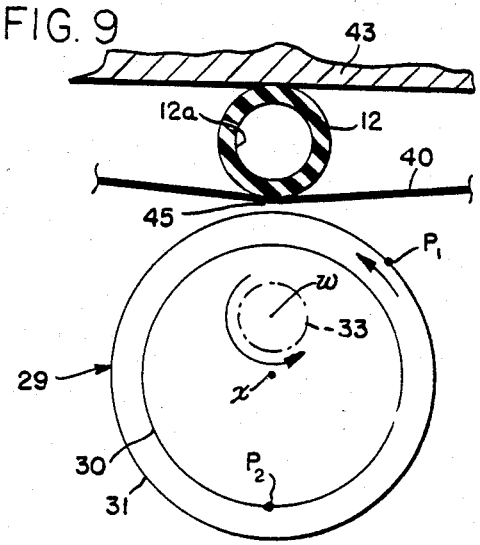

The linear zone or band of contact z between tube 12 and membrane 40 is clearly shown in FIGS. 6-9. Similarly, the linear zone or band of contact y between the membrane and the outer race is revealed in FIGS. 6-8; however, when the inner race of the bearing assembly has rotated into a position where its center x approaches maximum spacing from platen 43, a gap or spacing 45 develops between outer race 31 and membrane 40 (FIG. 9). The gap assures that tubing 12 will not be restrained by the bearing assembly from assuming a condition of maximum lumen cross sectional area, and also allows incremental angular advancement of the outer race 31.

The incremental angular advancement may be observed by noting the relative positions of reference points $P_1$ and $P_2$ along the outer and inner races. In FIG. 6, such points are shown to be in radial alignment. As the drive shaft rotates 90° about axis w, reference point $P_2$ has shifted 90° in a counterclockwise direction while $P_1$ retains its original position because rotation of the outer race is resisted by contact with membrane 40. In FIG. 8, points $P_1$ and $P_2$ are 180° apart with $P_1$ still remaining in its original position. However, as the inner race rotates from the position depicted in FIG. 8 towards the position of FIG. 9, the outer race 31 moves out of contact with membrane 40 and the slight frictional resistance inherent in the operation of assembly 29 causes outer race 31 to rotate along with inner race 30. Point $P_1$ therefore shifts a limited angular distance from its original position and will continue such movement until the outer race again contacts membrane 40 in approaching the position of FIG. 6. When the FIG. 6 position is again assumed, however, reference points $P_1$ and $P_2$ will no longer be in radial alignment but will be separated a limited angular distance from each other.

FIG. 10 illustrates a construction which is identical to those already described except that membrane 40' has a multiplicity of flexible but non-stretchable reinforcing elements 45 extending along the plane of the membrane in a direction perpendicular to bands of contact y and z. The embedded filaments may be formed of Dacron, wire, or any other suitable material, and prevent lateral stretching of the membrane without appreciably affecting expansion and contraction of the membrane in the general direction of the lines of contact. The preferential reinforcement of the membrane insures that frictional resistance inherent in the construction of bearing assemblies will not in any case be transmitted through the membrane to cause lateral displacement of tube 12 and possible variation in the delivery rate of the pump apparatus. Such reinforcement, while generally unnecessary, may become important in pumps of larger capacity in which the tubing is relatively large (e.g., more than 1 cm. OD) and of substantial wall thickness.

In the operation of the embodiments of FIGS. 1-10, rotation of shaft 33 causes a progressive occlusion of the tube 12 in a downward direction as each bearing assembly in downward sequence assumes the tube-collapsing position depicted in FIG. 4. (It will be understood that if the direction of shaft rotation were reversed, the progressive action of the bearing assemblies would similarly be reversed to drive a segment of fluid upwardly rather than downwardly.) FIG. 3 shows the uppermost bearing assembly of the series in the tube-occluding position of FIG. 4. The next tube bearing assembly directly below it is advancing into occluding positions, the middle assembly is in its maximally open position of FIG. 5, and the remaining three bearing assemblies therebelow are progressing towards their maximally open positions. A metered segment of fluid is thereby forced downwardly through the tube in the direction of peristaltic action.

FIGS. 11-15 depict a preferred embodiment of the invention similar to the embodiments already described except that tube 112 is part of a replaceable casette 100. If the apparatus is to be used for the administration of parenteral fluids, then the casette may include a suitable coupling 113 at one end of the tube, the coupling being equipped with a spike and drip chamber as previously indicated, and the upper portion of the tube also being equipped (if desired) with a control device 116 similar to device 16. The opposite end of the tube is provided with a suitable connector 117 which, if the apparatus is to be used for parenteral administration, would take the form of a needle or cannula.

The mid-portion of tube 112 is stretched slightly across the opening 150 of a rigid perimetric frame 151. The frame is generally planar and may be provided with inner and outer flanges 152 and 153 for increased rigidity. To facilitate mounting the tube 112 upon the frame 151, the tube may be formed in sections, with mid-section 112a having its ends secured to rigid mounting sleeves 154 and 155. The sleeves are provided with wing portions 156 that are permanently secured by heat sealing, fusion bonding, or any other suitable means to the portions of frame 151 above and below window opening 150. The upper section 112b of the elastomeric tubing has its lower end secured to the rigid sleeve 154, and the lower section of the tube has its upper end similarly secured to lower sleeve 155.

As shown in FIG. 11, platen 43 and facing 44 are mounted on door panel 20 and are dimensioned to extend through opening 150 of casette frame 151 when the casette is in operative position and the door is latched closed. When the casette is in operating position, locating pin 157 of the housing extends through aperture 158 in the upper portion of the frame 151. Tube section 112a engages membrane 28 and is supported or braced by planar platen 43 and its resilient facing 44 in the same manner as shown and described with respect to FIGS. 3-10. However, the casette 100 greatly facilitates use of the apparatus, particularly in medical applications, because it may be discarded in its entirety after it has served its purpose, and a new sterile casette may be inserted into position for use by the same patient or a different patient, without risks of cross contamination and without need to clean and sterilize the used casette or the pump housing and mechanism.

The ease and speed with which a casette may be removed and replaced is of course of considerable importance, especially in medical applications where time may be critical. The casette also insures accurate alignment of the tensioned section 112a of the tube with respect to the rotational axis w of the drive shaft, a critical relationship as previously described in connection with FIGS. 3-10. Furthermore, the casette 100 allows precise tensioning or stretching of the linear tube section 112a during manufacture of the casette. Since the extent of tensioning of the linear tube section affects the internal diameter of that section, reproducibility of flow rates may be assured.

In assembling the casette of this invention it has been found advantageous to perform the following steps to assure uniform stretching of tube section 112a. The tubing is first connected to sleeves 156 before the sleeves are attached to perimetric frame 151. The frame is mounted on a jig (not shown) utilizing the alignment aperture 158. The jig accommodates two conventional ultrasonic welding horns, and one of the horns is operated to weld one of the sleeves 156 to the frame. A weight capable of exerting a predetermined stretching force is attached to the other end of the tubing and the tubing is freely stretched by the weight. The other attachment sleeve 156, which has been connected to the tubing but has been allowed to float freely with regard to the frame, is then secured to the frame by the second ultrasonic welder. Accurate "inline" measurement of tubing inside and outside diameters is possible by means of laser micrometers, air gauges, or the like. If a deviation is detected then the extent of stretching may be readily adjusted by varying the weight used to produce such stretching. By such a procedure, stretching, tubing size, and pumping action may be accurately controlled. While ultrasonic welding has been found particularly effective, other means of attachment such as cementing, solvent bonding, or mechanical fastening may be used.

Should production operations result in variations in the inside diameters of the tensioned tube sections 112a of the casettes and not be corrected by stretching adjustment as described above, each casette may be coded with suitable indicia, colors, or indentations on the frame 151 or elsewhere to indicate the average ID of the tensioned tubular pumping section 112a of that particular casette, and the microprocessor of the pump mechanism may then be programmed accordingly to correct the pump speed to achieve the required delivery rate. If desired, the pump may be equipped with mechanical or electrooptical transducers for reading such coding automatically.

The frame 151 of the casette includes a tab portion 159 which projects beyond the door 20 when the door is closed and the casette is in operative position, thereby providing a clear visual indication that a casette is in place. In addition, tab portion 159 is easily gripped by a user to facilitate insertion and removal of a casette.

Depending on its intended use, the system may include safety functions to insure that unintended interruptions or changes in pump operation will not occur or at least will not pass undetected. For such purposes, the opening 150 in the casette frame, and the tensioned pump section 112a of the tube, are substantially longer than the series of bearing assemblies 29. When the casette is in place, the lower portion of tube section 112a bridges a pair of guides 160, 161 and extends between the emitter 162 and receiver 163 of an ultrasonic or photoptic bubble detector. Also, an occlusion detector 164 may contact a portion of the tube directly below, or on the discharge side, of the series of rotor bearing pump assemblies 29 to sense increases in back pressure that might be caused by kinking of the outlet section 112c of the tube, obstruction of needle 117, or any other reason. Since bubble detectors and pressure sensors are well known in the art and do not constitute elements of this invention, further discussion is believed unnecessary herein.

The rigid platen 43, resilient facing 44, and elastomeric tube 12 and 112a are all preferably formed of materials that have suffficient transparency to permit a user or operator to view the peristalsis of the tube and the movement of fluid therethrough through the platen. For that purpose, the platen 43 may be formed of glass or any rigid and adequately transparent polymeric material such as polymethyl methacrylate, polymethyl alphachloro acrylate, cyclohexyl methacrylate, and the like. The facing layer 44 and tube 12 and 112a are preferably formed of silicone rubber or polyurethane rubber, but any elastomeric material having similar properties may be used. The elastomeric material of membranes 40 and 40' may also be silicone rubber or polyurethane rubber but, since transparency of the membrane is not necessary, a variety of other elastomeric materials such as neoprene may be utilized.

While in the foregoing we have disclosed embodiments of the invention in considerable detail for purposes of illustration, it will be understood by those skilled in the art that many of these details may be varied without departing from the spirit and scope of the invention.

We claim:

1. A linear peristaltic pump apparatus comprising a housing having an opening therein; a shaft rotatably supported within said housing adjacent said opening; means for rotating said shaft; a series of bearing assemblies within said housing each having concentric inner and outer bearing members; said inner member being eccentrically mounted upon said shaft with the centers of said inner members being arranged to describe a helix about the axis of said shaft; an elastomeric membrane secured to said housing about said opening and covering said opening; said membrane extending along and tangentially engaging the outer members of said bearing assemblies along a first linear zone of contact; a casette removably and externally supported by said housing adjacent to said membrane and comprising a rigid frame and a generally straight section of elastomeric tubing supported thereby; means provided by said housing for orienting said frame with said section of tubing lying in the same plane as said first zone of contact; and platen means provided by said housing and engagable with said section of elastomeric tubing to urge the same into engagement with the opposite side of said membrane along a second linear zone of contact parallel with said first zone of contact.

2. The apparatus of claim 1 in which said rigid frame is perimetric and is provided with an opening; said generally straight section of tubing extending across said opening; and said platen means extending into said opening to urge said tubing section into engagement with said membrane when said apparatus is in operation.

3. The apparatus of claims 1 or 2 in which said generally straight section of elastomeric tubing is supported by said frame in predetermined axially stretched and tensioned condition.

4. The apparatus of claim 3 in which said casette is coded to indicate the average inside diameter of said stretched and tensioned section of tubing.

5. The apparatus of claim 2 in which said opening is generally rectangular and is elongated in a direction parallel with said section of tubing.

6. The apparatus of claims 1 or 2 in which said casette includes a pair of end sections of tubing extending axially from opposite ends of said generally straight section of tubing; and connecting means at the free end of one of said end sections for connection with a patient.

7. The apparatus of claim 6 in which said casette includes coupling means at the free end of the other of said end sections for fluid-transmitting coupling with a medical container.

8. The apparatus of claims 1 or 2 in which said section of elastomeric tubing is transparent.

9. The apparatus of claims 1 or 2 in which said means for orienting said casette comprises at least one locating pin provided by said housing and at least one aperture provided by said casette frame for receiving said pin.

10. A linear peristaltic pump apparatus comprising a housing having an opening therein; a shaft rotatably supported within said housing adjacent said opening; means for rotating said shaft; a series of bearing assemblies within said housing each having concentric inner and outer bearing members freely rotatable with respect to each other; said inner members being eccentrically mounted upon said shaft with the centers of said inner members being arranged to describe a helix about the axis of said shaft; an elastomeric membrane secured to said housing about said opening and covering said opening; said membrane extending along said series of bearing assemblies for tangential engagement with the outer members thereof along a first band of contact extending in the same plane as the axis of said shaft; a casette removably and externally supported by said housing adjacent to said membrane and comprising a rigid perimetric frame having an opening and a generally straight section of elastomeric tubing extending across said opening; said frame including rigid sleeve elements secured to said frame on opposite sides of said opening with said section of said elastomeric tubing having opposite ends thereof secured to said sleeve elements; means for orienting said casette with said section of tubing extending along the side of said membrane opposite from said bearing assemblies and in the same plane as said first band of contact and said axis of said shaft; and platen means provided by said housing and engagable with said section of elastomeric tubing for urging the same into engagement with said membrane along a second band of contact parallel with said first band of contact.

11. The apparatus of claim 10 in which said frame includes a tab portion that projects from said housing when said casette is in operative position.

12. The apparatus of claim 10 in which said means for orienting said casette comprises male and female locating means provided by said frame and said housing, said locating means being mated together when said casette is in operative position.

13. The apparatus of claim 10 in which said section of elastomeric tubing is transparent.

14. The apparatus of claims 10 or 13 in which said section of elastomeric tubing is axially stretched and tensioned to a predetermined extent.

15. The apparatus of claim 14 in which said casette is coded to indicate the average inside diameter of said stretched and tensioned section of tubing.

16. A disposable casette for use with a linear peristaltic pump having a housing equipped with at least one casette-locating pin disposed in close proximity to a pump mechanism covered by an elastomeric membrane and also having a door equipped with a platen aligned with said membrane when the door is closed, said casette comprising a rigid planar frame having a locating aperture for receiving the casette-locating pin of a pump housing for orienting said casette in relation to such housing, said frame also having an enlarged generally-rectangular opening for registration with the membrane and platen of a pump housing, a pair of rigid attachment sleeves provided by said frame on opposite edges of said opening, and a straight section of transparent elastomeric tubing extending across said opening and having end portions immovably secured to said attachment sleeves, said attachment sleeves each being provided with a pair of outwardly-projecting wing portions permanently secured to said frame adjacent opposite edges of said opening.

* * * * *